United States Patent [19]

Malawer et al.

[11] Patent Number: 5,626,835
[45] Date of Patent: *May 6, 1997

[54] LOW VOC HAIR SPRAY COMPOSITION

[75] Inventors: Edward G. Malawer, Wayne; Kolazi S. Narayanan, Palisades Park, both of N.J.; James Cullen, Bartonsville, Pa.; Colleen M. Rocafort, Lake Hiawatha, N.J.

[73] Assignee: ISP Investments Inc., Wilmington, Del.

[*] Notice: The portion of the term of this patent subsequent to Jan. 5, 2015, has been disclaimed.

[21] Appl. No.: 255,192

[22] Filed: Jun. 7, 1994

[51] Int. Cl.$^6$ .................................................. A61K 7/11
[52] U.S. Cl. ................. 424/47; 424/78.02; 424/70.11; 424/DIG. 1; 424/DIG. 2; 514/957
[58] Field of Search ................. 424/47, DIG. 1, 424/DIG. 2, 78.02, 70.11; 514/957

[56] References Cited

U.S. PATENT DOCUMENTS 4,897,262  1/1990  Nandagiri et al. ............... 424/70.11
5,158,762  10/1992  Pierce ............................. 424/47
5,176,898  1/1993  Goldberg et al. ................ 424/47

OTHER PUBLICATIONS

Martino, G. T., et al. (1992). Spray Technology & Marketing, pp. 34–39.

*Primary Examiner*—Raj Bawa
*Attorney, Agent, or Firm*—Walter Katz; Marilyn J. Maue; Joshua J. Ward

[57] ABSTRACT

A low volatile organic compounds hair spray microemulsion in the form of a stable, clear, single phase system in which the particles therein have a diameter of less than 1 micron, consisting essentially of, by weight, (a) an ethyl half-ester of a copolymer of maleic anhydride and an alkyl vinyl ether in an amount of less than 20%, optionally neutralized up to 20 mole %, (b) an ethoxylated glycerol fatty acid ester as the surfactant having a hydrophobic-lipophilic balance of 10–18, in an amount of at least 0.1%, (c) ethanol in an amount of 55% or less, and (d) water to 100%.

21 Claims, No Drawings

LOW VOC HAIR SPRAY COMPOSITION

BACKGROUND OF THE INVENTION

1. Field of the Invention

This invention relates to hair spray compositions, and, more particularly, to low VOC hair spray compositions of a water-insoluble polymer in the form of a stable, clear, single phase system wherein substantially all particles therein have a diameter of less than 1 micron, i.e. a microemulsion.

2. Description of the Prior Art

Hair spray compositions generally are solutions of a hair fixative polymer and a solvent, usually ethanol, water or ethanol-water mixtures, such as described in U.S. Pat. Nos. 4,543,249; 4,923,694; 5,266,308; 5,085,859; 5,173,290; 5,176,898; and PCT WO 93/03705. Such compositions also may contain small quantities of one or more adjuvants normally found in cosmetic products including a small quantity of a surfactant. The presence of a surfactant in a hair spray composition reduces the surface tension between the aqueous and polymer phases in the composition, and provides sprays having a desirable small droplet size or mist. U.S. Pat. Nos. 4,543,249 and 5,176,898, for example, describe such a surfactant-containing system for water-soluble fixative polymers. Similarly, U.S. Pat. No. 5,085,859 discloses a hair treating composition containing a film-forming material which is an interpenetrating polymer network of a substituted vinyl copolymer having a polar functionality and a non-polar silsesquioxane. This patent suggests that the interpenetrating polymer might be incorporated into the composition as an emulsion or microemulsion; however, such formulations are not disclosed for an interpenetrating polymer, or for any other polymer.

Water-insoluble polymers, such as the ethyl and butyl half-esters of copolymers of maleic anhydride and methyl vinyl ether, known as GANTREZ®-ES resins, and sold by International Specialty Products (Wayne, N.J.), have been used for many years as the hair fixative resin of choice in alcohol-based hair spray compositions, both in non-aerosol (pump) and aerosol (propellant) delivery systems. Recent California state legislation, however, has required that future commercial hair spray compositions contain a low volatile organic compound (VOC) content therein, particularly 80% or less VOC (by 1994) and 55% or less VOC (by 1998). In order to meet the strict VOC standards, it has been necessary for hair spray formulators to substantially reduce the alcohol content and to substantially increase the water content of existing hair spray products. However, for water-insoluble polymers, such as GANTREZ®-ES resins, which do not dissolve readily in water-based systems, such changes produce two-phase systems, which is undesirable from a commercial standpoint.

Accordingly, it is an object of the present invention to provide a low VOC hair spray composition containing a water-insoluble polymer in the form of a clear, single phase system.

Another object of the invention is to provide a 55% or less VOC hair spray composition in the form of a clear, single phase system which includes a water-insoluble polymer, a surfactant and a solvent, and in which substantially all the particles therein have a diameter of less than 1 micron.

Still another object of the present invention is the provision of a stable, clear, single phase, water-based, 55% or less VOC pumpable or propellant-actuated hair spray composition including the ethyl half-ester of a copolymer of maleic anhydride and methyl vinyl ether as the hair fixative, a surfactant and alcohol.

A particular object of the invention is to provide a stable, clear, single phase hair spray composition of a water-insoluble fixative resin in the form of a microemulsion.

Still another object herein is to provide a hair spray concentrate of a water-insoluble hair fixative polymer in the form of a clear, viscous system and which, upon dilution with water and alcohol, will form a clear, single phase, low VOC hair spray composition in which substantially all the particles therein have a diameter of less than 1 micron.

These and other objects and features of the invention will be made apparent from the following more particular description of the invention.

SUMMARY OF THE INVENTION

A low VOC, preferably 55% or less, hair spray composition is provided herein which is a stable, clear, single phase system of a water-insoluble polymer in which substantially all the particles therein have a diameter of less than 1 micron, i.e. a microemulsion, preferably 0.1 micron or less, and optimally 0.05 micron or less, which comprises, by weight:

(a) a water-insoluble polymer, preferably the ethyl half-ester of a copolymer of maleic anhydride and methyl vinyl ether, optionally neutralized up to 20 mole %, preferably 5–15 mole %, and optimally 8–12 mole %, in an amount of less than 20%, preferably 2–10%, and optimally 4–6%;

(b) a surfactant, preferably a polyethoxylated glycol ether of glyceryl isostearate or monoleate, in an amount of at least 0.1%, preferably 0.2–2%, and optimally 0.5–1.5%;

(c) alcohol, preferably ethyl alcohol, in an amount of 55% or less, preferably 30–50%, and optimally 35–45%; and (d) water to 100%, preferably 38–67.8%, and optimally 47.5–60.5%.

Such low VOC hair spray compositions may be made by solvent dilution of a hair spray concentrate in the form of a clear, viscous liquid, comprising, by weight:

(a) a water-insoluble polymer in the amount of less than 55%, preferably 25–45%, and optimally 30–40%, (b) a surfactant in the amount of at least 0.5%, preferably 1.4–18%, and optimally 3–12%, and (c) alcohol to 100%, preferably 34–73.6%, and optimally 48–67%.

The low VOC hair spray compositions of the invention may be applied by a pump or propellant spray delivery system, preferably a pump system, as a fine spray having a good spray pattern. The fixative film thus-formed on the hair of the user exhibits the desirable performance characteristics of excellent long-term hold and high humidity curl retention, fast dry times and low tack.

DETAILED DESCRIPTION OF THE INVENTION

In the present invention, solubilization of a water-insoluble polymer, such as the ethyl half-ester of a copolymer of maleic anhydride and ethyl vinyl ether, into a low VOC, water-based hair spray composition which is a stable, clear single-phase system having a particle size of less than 1 micron in diameter, i.e. a microemulsion, is accomplished in the system herein by predetermining (1) the kind and amount of water-insoluble resin, (2) the kind and amount of surfactant, (3) the ratio of alcohol to water, and (4) the extent of neutralization of the water-insoluble polymer, as described below.

(1) Water-Insoluble Polymer

Suitable water-insoluble polymers for use herein include alkyl half-esters of copolymers of maleic anhydride and an alkyl vinyl ether. Such polymers have the general formula:

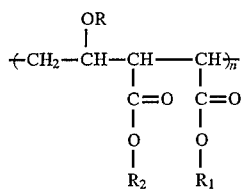

where $R=C_1-C_{18}$ alkyl, preferably methyl, $R_1=R_2=H$ or $C_1-C_{18}$ alkyl, preferably ethyl, at least one of $R_1$ or $R_2=H$, and n=50–1000, preferably 100.

One such polymer is GANTREZ® ES-225, which is available commercially as a 50% solution of the resin in ethanol. The commercial solution may be used directly to prepare the hair spray composition of the invention.

Suitably, the water-insoluble resin is present in an amount of up to 20% by weight of the composition, preferably 2–10%, and, optimally 4–6%.

(2) Surfactant

Suitable surfactants for use herein include ethoxylated glyceryl fatty acid esters, suitably with an HLB of >10, preferably about 12–18, and optimally about 14–16, and containing about 5–50 ethylene oxide (EO) units, preferably 15–35, and optimally about 20–30.

The alkyl group of the fatty acid ester suitably includes about 10–18 carbon atoms, saturated or unsaturated, e.g. stearyl, isostearyl, oleyl, etc. Tagat® I (PEG-30 glyceryl isostearate) (Goldschmidt) or Tagat® 02 (polyoxyethylene glycerol monoleate) surfactant compounds are preferred. Other suitable surfactants include ethoxylated natural wool fat, e.g. Ethoxylan® 1686 (PEG 75 lanolin); and a quaternized lanolin such as Lanoquat® 1751A.

Mixtures of surfactants also may be used herein. Accordingly the compound cocoamidopropyl betaine (Velvetex® Blc 35) may be used as a cosurfactant.

The surfactant is present in an amount of at least 0.1%, preferably 0.2–2%, and, optimally 0.5–1.5%, of the composition.

(3) Alcohol

Ethanol is present in the composition in an amount of 55% or less, preferably 30–50%, and, optimally 35–45%, corresponding to a VOC of 55% or less.

Water

Water is present to 100% of the composition, preferably 38–67.8%, and, optimally 47.5–60.5%.

(4) Neutralization of Water-Insoluble Polymer

Suitable neutralizing agents include aminomethylpropanol (AMP), dimethylstearylamine (DMSA), tertiary-isopropanolamine (TIPA), didodecylamine (DDA) and triethanolamine (TEA).

The water-insoluble polymer may be neutralized, if desired, to an extent of up to 20 mole % of the polymer, preferably 5–15 mole %, and, optimally 8–12 mole %.

The hair spray compositions of the invention exhibit those physical characteristics indicative of a microemulsion, that is, a stable, clear, single phase system in which substantially all the particles therein have a diameter of less than 1 micron, preferably less than 0.1 micron, and, optimally less than 0.05 micron.

The hair spray composition of the invention may be made by solvent dilution from a hair spray concentrate which is a stable, clear, viscous liquid, comprising, by weight:

(a) a water-insoluble polymer in the amount of less than 55%, preferably 25–45%, and optimally 30–40%;

(b) a surfactant in the amount of at least 0.5%, preferably 1.4–18%, and optimally 3–12%; and (c) alcohol to 100%, preferably 34–73.6%, and optimally 48–67%.

The low VOC hair spray compositions of the invention may be applied by a pump or propellant spray delivery system, preferably a pump system, as a fine spray having a good spray pattern. The fixative film thus-formed on the hair of the user exhibits the desirable performance characteristics of excellent long-term hold and high humidity curl retention, fast dry times and low tack.

Working examples of the invention and their performance during use are given in Table 1 below. The results were obtained using a Seaquist Euromist II pump spray system capable of delivering a 140–160 μl output from an actuator of 0.018"×0.010" deep. The pH of the compositions was 4.89–4.97.

TABLE 1

| Comp. No. | Wt. Gantrez® ES-225 (as solid) | Surfactant | Wt. of Surfactant | Wt. Ethanol | Wt. Water | Neutralizing Agent | Wt. Neutralizing Agent | Appearance of Composition |
|---|---|---|---|---|---|---|---|---|
| 1 | 5.0 | Tagat 02 | 1.24 | 39.80 | 53.50 | DDA | 0.46 | Clear |
| 2 | 5.0 | Tagat I | 1.24 | 45.15 | 48.14 | TIPA | 0.47 | Clear |
| 3 | 5.0 | Tagat I | 1.25 | 39.90 | 53.63 | AMP | 0.22 | Clear |
| 4 | 5.0 | Tagat I | 1.25 | 39.83 | 53.55 | TEA | 0.37 | Clear |
| 5 | 5.0 | Tagat I | 1.24 | 49.89 | 43.65 | AMP | 0.22 | Clear |
| 6 | 5.0 | Tagat I | 1.24 | 49.59 | 43.42 | DMSA | 0.75 | Clear |
| 7 | 5.0 | Tagat I | 1.24 | 49.75 | 43.54 | TIPA | 0.47 | Clear, particle size 0.01μ–0.2μ |
| 8 | 5.0 | Tagat I | 1.25 | 39.90 | 53.63 | AMP | 0.22 | Clear, pH 4.97 |
| 9 | 5.0 | Tagat I | 1.24 | 39.79 | 53.50 | TIPA | 0.47 | Clear, pH 4.89; partical size 0.01μ–0.02μ |
| 10 | 9.85 | Tagat I | 1.23 | 49.26 | 38.18 | DMSA | 1.48 | Clear |
| 11 | 14.67 | Tagat I | 1.22 | 48.90 | 33.00 | DMSA | 2.21 | Clear |
| 12 | 5.0 | Tagat 02 | 1.25 | 39.83 | 53.55 | TEA | 0.37 | Clear |

TABLE 1-continued

| Comp. No. | Wt. Gantrez ® ES-225 (as solid) | Surfactant | Wt. of Surfactant | Wt. Ethanol | Wt. Water | Neutralizing Agent | Wt. Neutralizing Agent | Appearance of Composition |
|---|---|---|---|---|---|---|---|---|
| 13 | 9.93 | Tagat O2 | 1.24 | 39.71 | 48.39 | TEA | 0.73 | Clear |
| 14 | 5.0 | Ethoxylan 1686 | 1.25 | 49.96 | 43.32 | TIPA | 0.47 | Clear |
| 15 | 5.0 | Velvetex* BK35 and Ethoxylan** 1686 | 0.22*** 0.31*** | 49.96 | 44.04 | TIPA | 0.47 | Clear |
| 16 | 5.0 | Tagat I and Ethoxylan 1686 | 0.62* 0.62* | 39.79 | 53.5 | TIPA | 0.47 | Clear |
| 17 | 5.0 | Tagat O2 and Ethoxylan 1686 | 0.62* 0.62* | 39.79 | 53.5 | TIPA | 0.47 | Clear |
| 18 (Control) | 5.0 | — | | 40.6 | 54.4 | — | — | 2-phase system; insoluble solid separated at 20° C.; cloudy at 30° C. |
| 19 (Control) | 5.0 | — | | 40.65 | 54.2 | TIPA | 0.15 | 2-phase system; insoluble solid separated at 20° C.; cloudy at 30° C. |
| 20 (Control) | 5.0 | — | | 40.5 | 54.3 | AMP | 0.20 | 2-phase system; insoluble solid separated at 20° C.; cloudy at 30° C. |
| 21 | 5.0 | Tagat I | 1.25 | 40.13 | 53.62 | — | — | Clear |

FOOTNOTES TO TABLE 1
*Velvetex is 37% active; available as 37% aqueous solution.
**Ethoxylin 1686 is 50% active; available as 50% aqueous solution.
***As 100% solid.
Clear means a single phase, optically clear water-like system and, free of haze.
Cloudy means visually, opaque with or without separation of crystals or oil droplets showing haziness.

Table 2 below provides concentrates for making the end-use hair spray compositions of the invention upon dilution of a given concentrate formulation with a predetermined mixture of ethanol and water. The concentrates were prepared with a suitable neutralizing agent, e.g. AMP or TIPA, at a 10% mole % degree of neutralization.

TABLE 2

| | Concentrate | | | |
|---|---|---|---|---|
| Ingredient | 8C-1 | 8C-2 | 9C-1 | 9C-2 |
| Gantrez ® ES-225 (as solid) | 40 | 35 | 40 | 35 |
| Neutralizing agent, (AMP/TIPA) | 1.76 (AMP) | 1.54 (AMP) | 3.78 (TIPA) | 3.31 (TIPA) |
| Tagat I | 10.0 | 8.75 | 10.0 | 8.75 |
| Ethanol | 48.24 | 54.71 | 46.22 | 52.94 |
| Total | 100.00 | 100.00 | 100.00 | 100.00 |

For example, hair spray compositions Nos. 8 and 9 in Table 1 were made from the concentrates of Table 2 in the following manner:

TABLE 2A

| Ingredient | To Obtain Comp. No. 8 from 8C-1 | To Obtain Comp. No. 8 from 8C-2 | To Obtain Comp. No. 9 from 9C-1 | To Obtain Comp. No. 9 from 9C-2 |
|---|---|---|---|---|
| Concentrate | 12.5 | 14.3 | 12.5 | 14.3 |
| Ethanol | 33.97 | 32.17 | 34.22 | 32.43 |
| Water | 53.53 | 53.53 | 53.28 | 53.27 |
| Total | 100.00 | 100.00 | 100.00 | 100.00 |

Concentrate formulations also can be provided without any neutralizing agent therein as shown in Table 3 below. The end-use hair spray compositions then can be prepared by dilution with a suitable amount of aqueous/ethanolic solution based upon the predetermined level of resin in the concentrate. The desired level of neutralization then can be provided by thereafter adding a suitable amount of the neutralizing agent.

TABLE 3

| | Concentrate | |
|---|---|---|
| Ingredient | 8/9C-3 | 8/9C-4 |
| Gantrez ® ES-225 (50% solution in ethanol - ISP) | 70 [solid resin-35] | 80 [solid resin-40] |
| Neutralizing agent | — | — |
| Tagat I | 8.75 | 10.0 |
| Ethanol | 21.25 | 10.0 |
| Total | 100.00 | 100.00 |

Table 4 below shows the advantageous performance of the hair spray compositions of the invention during use under standard test conditions. The results are shown for hair spray compositions 8 and 9 in Table 1.

TABLE 4

Performance of Hair Spray Compositions of Invention

| | Composition No. | |
|---|---|---|
| Characteristic | 8 | 9 |
| Film clarity | Clear | Clear |
| Film hardness | H | H |
| Long term hold - 90 min (%) | 95.86 | 92.81 |
| Dry time (sec.) | 73 | 79 |
| Duration of tack (sec.) | 44 | 47 |
| Stiffness | 7.0 | 7.6 |
| Non-flaking | 9.6 | 9.4 |
| Combability | 9.0 | 7.2 |
| Removability | Acceptable | Acceptable |
| Pump spray droplet particle size (μ) | 103.00 | 97 |
| Pump spray pattern (in.) | 3–3½ | 3–3½ |
| Pump spray pattern | Fine | Fine |

While the invention has been described with particular reference to certain embodiments thereof, it will be understood that changes and modifications may be made which are within the skill of the art. Accordingly, it is intended to be bound only by the following claims, in which:

What is claimed is:

1. A low volatile organic compounds hair spray concentrate microemulsion in the form of a stable, clear, single phase system in which the particles therein have a diameter of less than 1 micron, consisting essentially of, by weight, (a) an ethyl half-ester of a copolymer of maleic anhydride and an alkyl vinyl ether in an amount of less than 20%, optionally neutralized up to 20 mole %, (b) an ethoxylated glycerol fatty acid ester as the surfactant having a hydrophobic-lipophilic balance of 10–18, in an amount of 0.2% to 2%, (c) ethanol in an amount of 55% or less, and (d) water to 100%.

2. A hair spray microemulsion according to claim 1 wherein (a) is 2–10%, and 5–15 mole %, (b) is 0.2–2%, (c) is 30–50%, and (d) is 38–67.8%.

3. A hair spray microemulsion according to claim 1 wherein (a) is 4–6% and 8–12 mole %, (b) is 0.5–1.5%, (c) is 35–45%, and (d) is 47.5–60.5%.

4. A hair spray microemulsion according to claim 1 wherein the particle size is 0.1 micron or less.

5. A hair spray microemulsion according to claim 1 wherein the particle size is 0.05 microns or less.

6. A hair spray microemulsion according to claim 1 wherein (a) is the ethyl half-ester of a copolymer of maleic anhydride and methyl vinyl ether.

7. A hair spray microemulsion according to claim 1 wherein (b) is a polyethoxylated glyceryl fatty acid ester.

8. A hair spray microemulsion according to claim 7 wherein (b) has an hydrophilic-lipophilic balance of 12–18.

9. A hair spray microemulsion according to claim 7 wherein said balance is 14–16.

10. A hair spray microemulsion according to claim 7 wherein (b) has 5–50 ethylene oxide units.

11. A hair spray microemulsion according to claim 7 wherein (b) has 15–35 ethylene oxide units.

12. A hair spray microemulsion according to claim 7 wherein (b) has 20–30 ethylene oxide units.

13. A hair spray microemulsion according to claim 7 wherein (b) of the fatty acid ester has 10–18 carbon atoms.

14. A hair spray microemulsion according to claim 7 wherein (b) is the polyethylene glycol ether of glyceryl isostearate.

15. A hair spray microemulsion according to claim 7 wherein (b) is polyoxyethylene glycerol monoleate.

16. A hair spray microemulsion according to claim 1 wherein (a) has the formula:

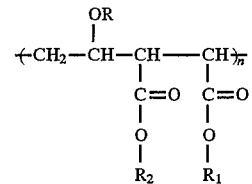

where

R=$C_1$–$C_{18}$ alkyl, $R_1$=$R_2$=H or $C_1$–$C_{18}$ alkyl, at least one of $R_1$ or $R_2$=H, and n=50–1000.

17. A hair spray microemulsion according to claim 16 in which n is 100.

18. A hair spray concentrate according to claim 1 wherein (a) is the ethyl half-ester of a copolymer of maleic anhydride and methyl vinyl ether.

19. A hair spray concentrate according to claim 18 in which (a) is neutralized up to 20 mole %.

20. A hair spray concentrate according to claim 1 wherein (b) is an ethoxylated glyceryl fatty acid ester with 5–50 ethylene oxide units, and the fatty acid ester has 10–18 carbon atoms.

21. A hair spray concentrate according to claim 20 in which (b) is polyethylene glycol-30 glyceryl isostearate or monoleate.

* * * * *